United States Patent
Keller

[11] Patent Number: 6,060,073
[45] Date of Patent: *May 9, 2000

[54] ARTIFICIAL FINGERNAIL METHOD AND COMPOSITION

[76] Inventor: Alexander M. L. Keller, 130 Oxford St., Brooklyn, N.Y. 11235

[ * ] Notice: This patent is subject to a terminal disclaimer.

[21] Appl. No.: 09/100,744

[22] Filed: Jun. 19, 1998

Related U.S. Application Data

[60] Division of application No. 08/858,913, May 19, 1997, which is a continuation-in-part of application No. 08/710,491, Sep. 18, 1996, abandoned, which is a continuation-in-part of application No. 08/530,886, Sep. 19, 1995, Pat. No. 5,632,973.

[51] Int. Cl.[7] .............................. A61K 6/00; A61K 7/00; A61K 7/04
[52] U.S. Cl. ............................................. 424/401; 424/61
[58] Field of Search ........................................ 424/401, 61

[56] References Cited

U.S. PATENT DOCUMENTS

5,632,973  5/1997  Keller ........................................ 424/61

Primary Examiner—Thurman K. Page
Assistant Examiner—Sharon Howard
Attorney, Agent, or Firm—Steven Horowitz

[57] ABSTRACT

Novel composition and method for forming artificial fingernails in situ and for prefabricated nails for people with weak, damaged nails. A vinyl fingernail extension is adhered to the top surface of the free end of a natural fingernail. Then for the in situ nail a coating of cyanoacrylate adhesive is applied to the vinyl extension and the natural nail. For the prefabricated nail, a fill in preliminary coating on the natural nail is first employed. Afterwards layers of a pink mixture in powder form of between approximately 8 and 12 parts by volume acrylic ester polymer or copolymer and 1 part sodium bicarbonate is applied to the adhesive coating while still wet to create an instant hardening. The coatings are repeated several times. The resulting nail looks naturally pink, blends into its finger, skin and nail environment, is hardy, corrects broken nails and is strong enough to protect against further damage to nails. Main benefit is that individuals whose nails are weak or broken and could not otherwise grow long nails because of this can do so and since the vinyl absorbs the adhesive and acrylic mixture and hardens, the artificial nail of the present invention need only be reinforced approximately every four weeks, a treatment that does not involve reapplying any vinyl extension. The vinyl extension just grows off and never needs to be replaced. Other compounds including sodium sulfate, sodium carbonate or sodium borate are substitutes for sodium bicarbonate but the result will not be as good.

42 Claims, 2 Drawing Sheets

ARTIFICIAL FINGERNAIL METHOD AND COMPOSITION

This divisional application is file pursuant to 37 CFR Section 1.53(b) as a divisional application of application Ser. No. 08/858,913 filed May 19, 1997 which was filed pursuant to 37 CFR Section 1.53(b) as a continuation-in-part application of application Ser. No. 08/710,491 filed Sep. 18, 1996, abandoned, which in turn was filed pursuant to 37 CFR Section 1.53(b) as a continuation-in-part application of application Ser. No. 08/530,886 filed Sep. 19, 1995, now U.S. Pat. No. 5,632,973.

BACKGROUND OF THE INVENTION

The present invention relates to artificial nails and in particular to a novel composition and method of applying and/or forming artificial nails. Artificial nails are well known and are used mainly by women but increasingly by men also in order to beautify, correct, strengthen and protect their natural fingernails. With regard to beauty, consumers want the appearance of long, smooth, nicely shaped fingernails and any artificial nail must not only be beautiful in itself but must also create the appearance of being natural and blend effectively into its natural environment, i.e. the natural nail and finger. With regard to protecting, correcting and strengthening nails, the biggest problem is that there are many people who simply cannot grow long nails, something they want very much to do. Another problem is that the artificial nails presently available do not last long. Another problem is the noxious odor and fumes caused by artificial nail products on the market. Still another problem is the inconvenience of needing to apply a primer of the nail product to the nail prior to the application of the nail product in order to "prime" or prepare the nail. A further problem is that the nail composition ingredients of the nail product to be applied yellows after awhile and has to be replaced. The ideal artificial nail product would strengthen the natural nail enough to permit the wearer to grow long durable nails thereby avoiding or correcting broken or weak nails and would do this without the above-mentioned disadvantages. Finally, any cosmetic product, particularly one that also has a protective function, is valuable only to the extent that it endures under normal conditions of wear and tear including cooking near flames and applying acetone based nail polish remover, does not evoke allergic reactions, is odorless, relatively easy to use and is economical.

Artificial nails of the prior art can generally be categorized into two groups: (i) preformed or prefabricated nails that are glued onto the natural nail and (ii) artificial nails formed on the natural fingernail by the application of a liquid solution or an adhesive composition to the natural fingernail referred to as in situ, on site or custom-fitted nails.

The prior art contains numerous examples of prefabricated artificial nails, such as those described and claimed in U.S. Pat. Nos. 2,633,139; 2,746,460; 2,764,166; 2.941,535,; 2,979,061; 3,037,514; 3,157,912; 3,277,900; 3,425,426; 3,483,289; 3,487,831; 3,552,401 and 4,106,614. Unfortunately, preformed nails of the prior art have significant disadvantages. Since they are not custom-made for every size and shaped finger, they rate poorly in terms of beauty since they do not look natural or blend effectively into their natural environment. In addition, they are not particularly effective at strengthening or protecting the nail and fall off fairly easily, thereby necessitating constant replacement. Preformed nails are often made out of hard plastic. An example of the material they are made out of is ABS plastic.

Accordingly, most beauty professionals employ the kind of artificial nails that are formed in situ. Even in this category, however, there are no methods or compositions that are entirely satisfactory even though it is also known in the art to apply a coating of adhesive to the top surface of a natural fingernail and to the top surface of a fingernail extension in situ. For one thing, applying this kind of artificial nail is time consuming in that one has to repeatedly visit a cosmetician and expend time while she forms the artificial nail in situ (directly on the nail). Most artificial fingernails formed in situ do not last longer than approximately one week and therefore require constant repeat visits. Furthermore, the fact that the wearer never knows when it will fall off and need immediate replacement can create embarrassment and discomfort. In addition, most artificial nails of this kind, while they look more natural than prefabricated nails, do not fully blend in with the finger and are not totally natural looking. In addition, the artificial fingernails that are formed in situ employ a form, usually plastic, around which the composition is applied and allowed to harden. The result is a less than perfect integration of the plastic form with the hardened composition and a less than perfect integration with the natural fingernail. Since the plastic form, which is usually placed on the tip of the nail, does not absorb the adhesive and is not integrated into the hardened composition to become one piece, there is no integrated whole nail created and if the plastic form comes off, the hardened composition will remain and the wearer will seem to have half a nail, or a nail of two different thicknesses. Finally, these artificial nails are not generally hard enough to adequately protect the nail from further damage or from separating and falling off the natural nail. Therefore, they do not allow the growth of long nails.

There are two other well known important disadvantages of prior art prefabricated artificial nails and prior art custom-fitted nails. The first is that the nails tend to catch on fire instantly when the wearer is cooking near a flame. The second is that artificial nail wearers like to clean them by removing nail polish thereon, often once a week, and the preferred materials for nail removal tend to contain acetone but the prior art artificial nails tend to melt when washed with acetone based solutions after approximately 30 seconds.

The fact of the matter is that there is great need among women and men for an artificial nail that looks natural, is hardy, strengthens and corrects broken nails and protects against further damage to nails so as to permit someone who cannot otherwise grow long beautiful nails to do so. Furthermore, there is a need for an artificial nail product that is odorless, is easy to use in that it does not require a primer and is made of non-yellowing ingredients. Finally, there is a need for an artificial nail product that is fire retardant and does not melt easily when washed with acetone-based nail polish removers.

SUMMARY OF THE INVENTION

The primary objective of the present invention is to accomplish all of the above objectives thereby making artificial fingernails a much more valuable product. In particular, it is an object of the present invention to provide a method of forming artificial fingernails that has the pinkish color of natural nails and blends in perfectly with the natural fingernail as well as the mold used to form it.

It is also an object of the present invention to provide an artificial nail product of the prefabricated type that has the pinkish color of natural nails and blends in perfectly with the natural fingernail.

It is an object of the present invention to provide an artificial fingernail extension made substantially of approximately 10 mils thick frosty clear, firm polyvinyl chloride that can absorb the cyanoacrylate adhesive mixed with the acrylic powder and hence be integrated into one piece.

It is an object of the present invention to provide a method of applying a vinyl fingernail extension that absorbs the cyanoacrylate adhesive mixed with the acrylic powder and hardens into one piece so that the vinyl extension eventually grows off and never needs to be replaced provided reinforcement treatments applying the adhesive and acrylic mixture are followed.

It is an object of the present invention to provide a method of shielding nails by applying cyanoacrylate adhesive and an acrylic powder mixture with sodium bicarbonate.

It is an object of the present invention to provide a method of mending cracked or broken nails by applying a vinyl patch over the cracked area or broken area and whereby the vinyl absorbs the cyanoacrylate adhesive and acrylic powder containing sodium bicarbonate and hardens into one piece.

It is an object of the present invention to employ a nail composition that contains a mixture of sodium bicarbonate and acrylic powder.

It is an object of the present invention to employ a nail composition that involves the procedure of adhering a vinyl fingernail extension to the top surface of a free end of the natural fingernail, applying a coating of cyanoacrylate adhesive to the top surface of both the natural nail and the vinyl extension and then applying on top of the adhesive a layer of a pink mixture in powder form of between 8 and 12 (ideally 10) parts by volume acrylic ester polymers and 1 part sodium bicarbonate to the top surface of both the natural fingernail and the vinyl extension while the adhesive coating is still wet in order to cause instant hardening.

It is a further object of the present invention to employ the above procedure using a vinyl fingernail extension that is between 8 and 12 mils thick, where the mixture that has between 8 and 12 parts by volume acrylic ester polymer and 1 part sodium bicarbonate optionally has a reddening agent, the mixture is applied by spraying from a (non-aerosol or aerosol) container, the cyanoacrylate adhesive is industrial or medical grade adhesive of medium viscosity comprising ethyl cyanoacrylate and a minute amount of preservative.

It is a further object of the present invention to employ the above procedure so as to create four coatings on top and two on the underside of the nail while brushing off excess powder before each repetition and shaping and filing the resulting fingernail surface.

It is a further object of the present invention to employ the above procedure using sodium sulfate, sodium carbonate or sodium borate to be mixed with the acrylic ester polymer instead of sodium bicarbonate.

It is an object of the present invention to employ a nail composition that utilizes the above composition and method wherein the acrylic ester polymers powder contain benzoyl peroxide catalyst, reddening agent (optional) and opaquing agents such as titanium dioxide and silicon dioxide.

It is an object of the present invention, whether for custom-fitted ("in situ") nails or prefabricated nails to employ a nail composition that utilizes an industrial cyanoacrylate adhesive that is applied to the natural fingernail as well as to the vinyl extension and whereupon the acrylic powder mixture containing sodium bicarbonate is sprayed onto the entire nail.

It is an object of the present invention to employ a nail composition and method such that the wearer's natural fingernail that was weak and prone to breaking is strengthened and can grow long beautiful nails.

It is an object of the present invention to employ a nail composition and method such that the wearer's natural fingernail that was weak and prone to breaking can grow long beautiful nails requiring only reinforcement treatments every three to four weeks.

It is an object of the present invention to employ a nail composition in conjunction with a prefabricated nail that involves the procedure of adhering a prefabricated vinyl fingernail extension to the top surface of a free end of the natural fingernail or to the entire top surface of the natural fingernail, applying a coating of cyanoacrylate adhesive to the remaining top surface, if any, of the natural nail and then applying one or more layers of a pink mixture in powder form of between 8 and 12 (ideally 10) parts by volume acrylic ester polymers and 1 part sodium bicarbonate to the top surface of both the natural fingernail and the vinyl extension while the adhesive coating is still wet in order to cause instant hardening.

It is a further object of the present invention to employ the above procedure using a prefabricated vinyl fingernail extension that is between approximately 6 mils and 10–50 mils thick, where the mixture that has between approximately 8 and 12 parts by volume acrylic ester polymer and 1 part sodium bicarbonate has a reddening agent (optional), the mixture is applied by spraying from a (non-aerosol or aerosol) container, the cyanoacrylate adhesive is industrial or medical grade adhesive of medium viscosity comprising ethyl cyanoacrylate and a minute amount of preservative.

It is a further object of the present invention to employ the above procedure so as to create one to four coatings on top and an optional coating on the underside of the nail formed with the prefabricated nail while brushing off excess powder before each repetition and shaping and filing the resulting fingernail surface.

It is a further object of the present invention to employ the above procedure in conjunction with a prefabricated nail using sodium sulfate, sodium carbonate or sodium borate to be mixed with the acrylic ester polymer instead of sodium bicarbonate.

It is an object of the present invention to employ a nail composition in conjunction with a prefabricated nail that utilizes the composition wherein the acrylic ester polymers powder contain benzoyl peroxide catalyst, reddening agent (optional) and opaquing agents such as titanium dioxide and silicon dioxide.

It is an object of the present invention to employ a nail composition in conjunction with a prefabricated nail that utilizes an industrial cyanoacrylate adhesive that is applied to the natural fingernail as well as to the vinyl extension and whereupon the acrylic powder mixture containing sodium bicarbonate is sprayed onto the entire nail.

It is also an object of the present invention to employ an artificial nail that is fire retardant and which does not melt easily when washed with acetone-based nail polish removers.

These and other objects of the present invention are accomplished in accordance with the method of the present invention.

THE MATERIALS—VINYL

An important novel feature of the present invention is the use of vinyl in an artificial nail composition in conjunction with the acrylic powder of the present invention. Another important novel feature of the present invention is the use of vinyl, namely polyvinyl chloride, as an artificial fingernail "platform" or foundation upon which to add various overlays. While prior art artificial nail compositions are made of hard plastic, silk or fiberglass, the fingernail extension of the artificial nail composition of the present invention is made of rigid polyvinyl chloride for the prefabricated nail and is made of firm (more flexible than rigid) polyvinyl chloride for the "in situ" or custom-fitted nail. Because of the nature of polyvinyl chloride, it is able to absorb the cyanoacrylate adhesive and acrylic powder mixture and permanently bond together to form hard nails. This permanent bond is not achieved by the temporary adherence of the artificial nail foundation to pressure sensitive adhesives mentioned in the prior art. The polyvinyl chloride fingernail extension may also be used as a platform to which may be added overlays of fiberglass, silk or linen of the prior art in accordance with any known method.

The vinyl is typically any polyvinyl chloride compound. The polyvinyl chloride for the custom-fitted fingernail extension, generally can have small amounts (low parts per million) of a plasticizer for flexibility or of another substance providing flexibility. For the prefabricated fingernail extension the polyvinyl chloride would generally not have a plasticizer but it may have plasticizer provided the tensile strength of 3,000 to 10,000 psi, described in detail below, is maintained. It is contemplated by the present invention that the rigid prefabricated polyvinyl chloride fingernail extension can be made by any suitable method including injection molding. Low amounts of a metallic stabilizer may be added if appropriate to the particular method of manufacture (e.g. if the polyvinyl chloride prefabricated fingernail extensions are made by injection molding they would probably not contain a metallic stabilizer).

One of the preferred colors is one that is known in the industry as frosty clear or matte clear. For the custom fitted nail method and composition, other colors of the polyvinyl chloride similar to this color may also work but not as well, although that is mainly a matter of taste. For the prefabricated nails, other colors of the polyvinyl chloride, such as "clear", white or other specific colors, but the result will not be as identical to natural nails. However, it is surely contemplated by the present invention that any other suitable color of the prefabricated polyvinyl chloride may be employed satisfactorily such as apricot, peach, clear, etc., depending on subjective issues of taste.

For custom fitted nails, the thickness of the vinyl can range from approximately 8 to 12 mils but 10 mils (i.e. 10 gauge) is ideal. A "mil" equals one thousandth of an inch in thickness of a plastic material, i.e. polyvinyl chloride fingernail extensions. For prefabricated nails the thickness of the vinyl can range from a low of approximately 6 mils, to a high of approximately 45–50 mils. It should be noted that it may be difficult to injection mold polyvinyl chloride to a thickness of less than 10 mils. The ideal thickness is a subjective matter of taste since it depends on the desired thickness of the resulting nail. If the prefabricated polyvinyl chloride were to be made from sheets of polyvinyl chloride between 6 and 10 mils, it may be possible and sometimes desirable to obtain thicknesses of approximately 8 mils (i.e. 8 gauge). If, however, as is more likely, the fingernail extension is made by injection molding the polyvinyl chloride, perhaps it can be said that the typical thickness is somewhere in the ballpark of 20 mils, give or take 10 mils (i.e. 10 to 30 mils). It should be noted that not only are these thicknesses very approximate but the thickness of the artificial nail is not necessarily uniform—there may be variations in thicknesses within the nail itself. For example, the prefabricated polyvinyl fingernail extension may be made to taper off in thickness at the ends of the fingernail extension.

The rigidity type for the prefabricated nail is known in the industry as "rigid". In particular, the prefabricated polyvinyl chloride should have a tensile strength of approximately between 3500 to 7000 psi, although suitable rigid fingernail extensions may also be found up to approximately 10,000 psi. The rigidity type for the custom fitted nail is known in the industry as "firm", which is more flexible than "rigid", i.e. it has a lower tensile strength.

Between 3 and 8 mils and between 12 and 20 mils for the thickness of the vinyl used for custom fitted nails will also work to some extent but not the way it is supposed to.

For the prefabricated nails, between 3 and 6 mils for the thickness of the vinyl used will also work to some extent but not the way it is supposed to. Accordingly, the present invention contemplates the possibility of using 3 to 8 or 12 to 20 mils thickness of vinyl for the custom fitted nail and 3 to 6 mils thickness of vinyl for the prefabricated nail, although the performance obtained from such a product may be reduced.

One important advantages of using polyvinyl chloride for the fingernail extension, as opposed to ABS plastic of the prior art, is that polyvinyl chloride taken alone will not instantly catch fire and is fire retardant. This is important since a common problem even for otherwise high quality artificial nail products is their tendency to immediately catch fire when the wearer is cooking near a flame, a common, if not a daily, occurrence. A second important advantage of using polyvinyl chloride for the fingernail extension, as opposed to ABS plastic of the prior art, is that the polyvinyl chloride nails of the present invention are not easily soluble in the most typically used material used for nail polish remover—acetone. Accordingly, when the wearer cleans her nails by removing the nail polish thereon, as is typically done once a week, the artificial nail of the present invention will not begin to dissolve from only 30 seconds of being washed in acetone-based nail polish remover, as is the case with ABS plastic. It would take approximately 4 to 6 times longer amounts of such exposure to acetone based nail polish remover for the polyvinyl chloride to dissolve than the length of time for the ABS plastic. A third advantage of polyvinyl chloride over ABS plastic is that that polyvinyl chloride is more color stable—ABS plastic changes in color over a period of months. In addition, because of the inherent nature of vinyl, it is odorless.

For custom-fitted nails, one of the advantages of polyvinyl chloride as the material for the fingernail extension over acetate plastic or other hard plastic used in the prior art is that the necessary thickness of ten mils can be maintained while at the same time retaining the soft pliability of the vinyl. In contrast, ten mil plastic is hard and not very pliable. In addition, plastic that is thin enough to be soft is not thick enough to develop into hard nails as occurs with the method of the present invention.

For the prefabricated nails, there may be other differences, in comparison with the custom fitted nail, such as in the shape of the nail extensions used in accordance with the method and composition of the present invention. First of all, the present invention contemplates that the size and shape of the prefabricated nail extension will vary with the style of the product or even with the individual's finger. For example, one option is to have the lower edge of the vinyl extension rounded in an arc shape, as shown in the figures herein, and another possibility is to have a straight edge, as with the custom fitted vinyl nail extension. The prefabricated nail extension can also vary with regard to how much of the natural fingernail is covered—from a little to the entire nail.

Figures 8, 9:
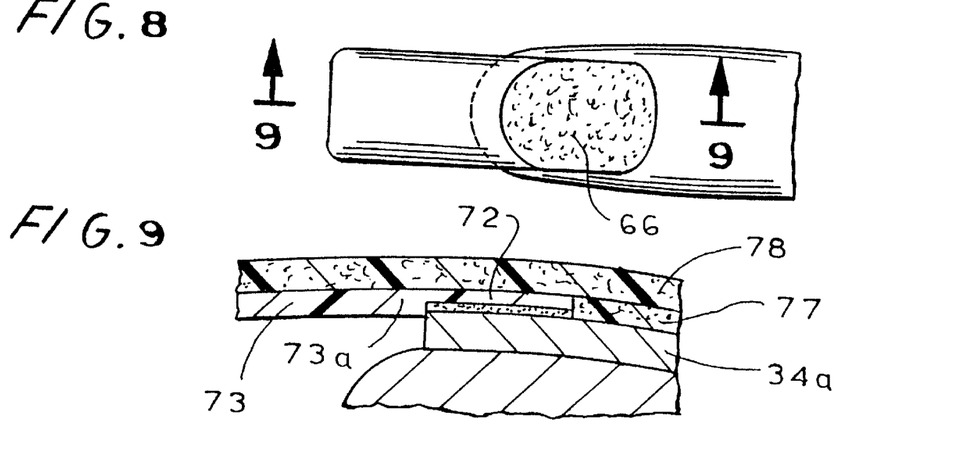
FIG. 8 is a top plan view of the prefabricated vinyl extension of FIG. 7A after the "fill in" layer of nail composition of the present invention has been applied to the natural nail.
FIG. 9 is an enlarged sectional view taken along line 9—9 of FIG. 8.

Another difference with the custom fitted nail is the possibility of not having a smoothed-down bottom edge of the extension for the prefabricated nail. For example, if the rounded bottom edge is used and the extension covers a relatively small portion of the natural fingernail, it is also likely, although not certainly not required by this invention that the portion of the extension that is above the natural nail be thinner than the remainder of the fingernail extension (i.e. thinner than 6 to 50 mils) and that the remaining portion of the extension—the part of the extension outward from the nail be of normal thickness (approximately 6 to 50 mils). In that case, to maintain the smooth evenness of the surface of the entire nail, the extra thickness of the remaining portion of the extension that extends outward from the finger would be underneath or below the surface of the extension, as described below and as depicted in FIG. 9.

THE ACRYLIC POWDER

The term "platform" is sometimes used herein to denote the material of the artificial fingernail extension. The term "overlay" is sometimes used to denote the powder, adhesive or other materials placed over the platform to create the full artificial fingernail.

As described in detail below, the present invention contemplates the use of a novel powder, in conjunction with adhesive, on the polyvinyl chloride fingernail extension to make the prefabricated and custom fitted nails. It should be noted, however, that one highly significant advantage of using polyvinyl chloride as the so-called platform on which to build the artificial nail, at least the prefabricated artificial nail of the present invention, is that numerous advantages are achieved even if the prior art overlay is used and even if the prior art methods of application are used. These advantages may be reaped even if any combination of other prior art materials such as the following are used as overlays: (i) the prior art acrylic powder with adhesive, (ii) urethane acrylate gels, photoactivated or epoxy gels, which do not require adhesive and (iii) fiberglass, silk or linen fabrics with adhesive.

The novel acrylic powder of the present invention employs a prior art acrylic powder together with sodium bicarbonate powder added to it. The standard acrylic powder to which the sodium bicarbonate is added may be any commercially available acrylic copolymer powder composition for fingernail preparations, optionally one containing a reddening agent, and in particular an acrylic ester copolymer composition that also contains benzoyl peroxide or similar polymerization initiator. Ideally, the acrylic powder composition will also have opaquing agents such as titanium dioxide and silicon dioxide as does the Odorless Pink Powder that is commercially available from OPI Products, Inc. of North Hollywood, Calif. The purpose of the acrylic powder in the mixture of acrylic powder and sodium bicarbonate is twofold: (i) to add pink pigmentation thereby duplicating the effect of a natural nail and (ii) to avoid making the nail so hard that it is difficult to buff. The proper proportion to accomplish this is between 8 and 12 and ideally 10 parts by volume of acrylic powder to 1 part sodium bicarbonate. In other words, if the proportion of sodium bicarbonate is too high in the powder mixture, (i.e. the acrylic powder is less than 8 parts per 1 part volume sodium bicarbonate) the resulting nail will contain white spots (even if the red dye has been added to the sodium bicarbonate). If the proportion is so off that the acrylic powder is less than 1 part per 1 part sodium bicarbonate the resulting nail would also be too hard thereby making it difficult to buff. If, on the other hand, the proportion of sodium bicarbonate is too low in the powder mixture, (i.e. the acrylic powder is more than 12 parts per 1 part sodium bicarbonate) the adhesive will be aesthetically acceptable but will not instantly dry and bond with the powder and vinyl. Finally, if the proportion of sodium bicarbonate is even lower in the powder mixture, (i.e. the acrylic powder is more than 15 parts per 1 part sodium bicarbonate), the powder functions like acrylic powder without any sodium bicarbonate and dries very slowly and bonds very slowly to the vinyl. Accordingly, the present invention contemplates the possibility of using 1 to 8 or 12 to 15 parts acrylic powder per 1 part sodium bicarbonate, although the performance obtained from such a product may be marginal.

It should be noted that it is contemplated that the acrylic powder used in the present invention need not be pink and that the use of pink powder rather than white powder is not required. The choice of the color of the powder may be affected by the subjectively chosen color of the nail desired or by other factors including the quality of the powder.

In an alternative embodiment of the acrylic powder mixture used in the method and composition of the present invention, sodium bicarbonate may be replaced with certain other weak bases, namely sodium carbonate, sodium borate or sodium sulfate or the following other compounds: aluminum stearate, ammonium acetate, sodium sesquicarbonate, aluminum hydroxide, sodium carboxyl methyl cellulose, sodium acetate and ammonium carbonate. The result will not be as good, however, aesthetically, in that the resulting nail will contain white spots as opposed to exhibiting an entirely natural and perfectly consistent light pink pigmentation. Accordingly, in this alternative embodiment, the ratio of 8 to 12 parts acrylic powder to 1 part sodium carbonate (or borate or sulfate) need not be adhered to conscientiously since the pigmentation will not be satisfactory anyway. Also, these other weak bases have larger granules and it is difficult to grind them into fine, homogeneous particles which is necessary in order to mix well with the acrylic powder.

One advantage of the acrylic powder of the present invention over certain prior art is that it is odorless, as are all the ingredients of the present invention. Sometimes, it is possible to see nail salons in which beauty professionals sit with white masks over their nose while serving customers. This is because the solutions used for forming the prior art nails have a powerful odor. This problem does not exist with the artificial nails of the present invention.

THE NEW METHOD

The following method is used for custom fitted nails. In Step One of the method of the present invention, the natural fingernail is prepared for the artificial nail extension. Any dead skin around the cuticles that extend over the natural nail is removed by routine methods such as by lightly drilling the cuticle area with a small diamond bit. Then, in Step Two, cyanoacrylate adhesive is applied to the free edge of the natural fingernail by means of a nail polish brush or similar applicator enough to cover the area where the vinyl extension will be placed, namely approximately one-third of the height of the natural nail. The cyanoacrylate adhesive used is any commercially available or medical grade medium viscosity (which is 20–60 cps although any viscosity between 3 and 150 cps will also work but not as well)

cyanoacrylate adhesive. The present invention is by no means limited to medium viscosity and other viscosities of cyanoacrylate adhesive may work as well under particular conditions.

An example of a commercially available medium viscosity industrial cyanoacrylate adhesive is Permabond 105 Industrial Adhesive manufactured by and available from Permabond International of Englewood, N.J. generally used for bonding to rubber and hard to bond plastics, having bond strengths of 2200–4000 psi, and made of ethyl cyanoacrylate. Permabond 105 is significantly more viscous than 5 Second Nail Glue™ or Krazy Glue™ and Permabond 105 has a roughly estimated viscosity of 30 to 40 cps at 25 degrees Centigrade/77 degrees Fahrenheit. An adhesive viscosity of between 20 and 60 cps is suitable for the present invention although any viscosity between 3 and 150 cps will work, although not as well. 40 cps is ideal if the container is fresh. The cyanoacrylate adhesive of the present invention also contains a minute amount of preservative which allows the bottle to last for a year. It is a colorless, transparent liquid. The adhesive of the present invention is odorless because of the inherent features of the adhesive and remains odorless when the powder of the present invention is applied.

In Step Three, following the application of the cyanoacrylate adhesive, a 12 inch long and ½ to ⅝ inch wide roll of the frosty clear, firm vinyl of the present invention made of polyvinyl chloride having a thickness of approximately 10 mils is placed on the top portion of the edge of the natural fingernail. The thickness of the vinyl can range from 8 to 12 mils but 10 mils is ideal. Between 3 and 8 and between 12 and 20 mils will also work to some extent but not the way it is supposed to. Using scissors, the vinyl is then cut off the roll and trimmed to fit the size of the fingernail tip. The bottom edge of the vinyl should extend over approximately one-third of the height of the natural nail. The bottom edge of the vinyl should generally correspond to an imaginary line connecting the endpoints of that section of the perimeter of the natural nail to which is attached the "whites" of the nail.

In Step Four, the bottom edge of the vinyl extension—the edge overlapping the natural nail—is then drilled with any commercially available device such as a carbide cutter or other appropriate electric nail drill with a hard bit so that there is no longer a bump on the fingernail at the beginning of the vinyl fingernail extension but rather a smooth surface at the transition point. As indicated above, the vinyl is typically any polyvinyl chloride compound with small amounts (low parts per million) of a plasticizer and a metallic stabilizer added.

Then, after dry, Step Five involves applying a first coating of cyanoacrylate adhesive on the entire nail surface (natural fingernail plus vinyl extension). Then while still wet, spray on to the entire nail surface a previously prepared mixture of standard pink acrylic powder with sodium bicarbonate having a ratio by volume of between eight (8) and twelve (12) parts (and ideally ten (10) parts) acrylic powder to 1 part sodium bicarbonate. It should be noted that the present invention contemplates that in all cases the spray of the mixture of the present invention can be non-aerosol or it can be aerosol.

The application of the acrylic powder mixture will cause an instantaneous bonding and hardening between the natural nail, the polyvinyl chloride, the cyanoacrylate adhesive above and below the vinyl and the acrylic powder mixture, a hardening and bonding not achieved by the prior art. This is why the artificial fingernail extension of the present invention is made substantially of polyvinyl chloride which can absorb the compound applied on it, that is the cyanoacrylate adhesive with the acrylic powder mixture.

Step Five is repeated 3 additional times over the entire nail and 2 additional times on the underside of the vinyl extension. It should be noted that while the above number of coatings presented is ideal and recommended for the best results, the number of coatings can be lessened for people who are seeking to accomplish as much as possible but at less (labor) cost. In other words, although doing the treatment with fewer coatings will result in poorer results, the fact that the materials and methods of the present invention are utilized will still result in a better result than the prior art.

Prior to each of these 5 additional repetitions, a large cosmetic brush is used to remove excess powder, the vinyl nail extension is shaped with electric nail drills and an exceptionally rough file (e.g. cosmetic file #8080) is used to file the nail.

Step Six involves filing and buffing the nail for smoothness using known cosmetic implements. Then a final coating of the cyanoacrylate adhesive of the present invention (without the acrylic powder) is applied over the entire top surface of the nail.

Method Used for Prefabricated Nail

The above method, after Step One and Step Two, is varied somewhat beginning at Step Three when prefabricated nails are employed. In general, with the prefabricated nail, there is more flexibility in how to employ the method of the present invention. First of all, the prefabricated vinyl extension is not cut off a roll but is manufactured in the desired shape to correspond to the different sized fingers of various individuals. Furthermore, Step Four is different and drilling to smooth down the lower edge of the extension may be unnecessary. It is contemplated by the present invention that the prefabricated vinyl extensions may, although not absolutely necessarily, be manufactured with a built in lower edge than is already smoothed down so that not much of a bump is created when the extension is on (before application of the composition of the present invention). Alternatively, it may be manufactured so that the whole part of the extension that covers the natural nail is thinner than normal (i.e. thinner than 6–10 mils or other chosen thickness).

In addition, unlike Step Five for the custom fitted nail, the first coating applied after the vinyl extension is adhered to the nail is only on the natural fingernail, not on the vinyl extension, and it is to "fill in" the natural nail to make it even and smooth with the surface of the vinyl extension. This "fill in" layer consists of applying the adhesive of the present invention followed by the powder of the present invention (while the adhesive is still wet), just as in Step Five for the custom fitted nail in accordance with the method of the present invention. The "fill in" layer is then followed up with the layer of the adhesive and powder of the present invention on the top surface of both the natural fingernail and the polyvinyl chloride fingernail extension. In addition, the initial "fill in" coating can be repeated as necessary to make the natural nail even and smooth with the surface of the vinyl extension.

In addition, the prefabricated vinyl extension is harder and less flexible by its nature than the custom fitted nail. Accordingly, fewer coatings of adhesive and powder over the nail may be necessary than with the custom fitted nail. Instead of 3 additional coatings, as with the custom fitted nail, the number of coatings will vary as necessary or preferred by the wearer—from 1 to 4 coatings. Moreover, the application of 2 coatings on the underside of the nail is optional for the prefabricated nail.

The resulting nail will be smooth and natural with the same pigmentation as a natural nail. Perhaps more importantly, with the method and composition of the present invention, the wearer will achieve a clear natural look without nail polish so that a viewer cannot discern the presence of an artificial nail extension. The nail will be very hard and will be one integrated unit wherein the vinyl extension, adhesive, acrylic and natural fingernail all combine to form an integrated, strengthened aesthetically pleasing natural looking nail of beautiful shape.

If this process is followed once a month, the wearer's natural nail will have been so strengthened and, if it had gaps, filled in perfectly, that she or he will be able to grow long beautiful nails even though before beginning the treatment she could not do so because the nails were too weak to ever get long and were not hardy and beautiful.

REINFORCEMENT TREATMENTS—NO VINYL APPLIED

In order to maintain the long beautiful nails of the present invention all that is necessary is to undergo reinforcement treatments approximately once a month. In these reinforcement treatments, no vinyl extension need ever be applied. Accordingly, the vinyl extension simply grows off the nail after approximately three months (a time period which varies with each individual's nail-growing speed). In the reinforcement treatments, the first step is to shorten the nail, if necessary, by drilling the tip of the nail with an electric nail drill. In the first or second reinforcement session the tip of the nail will necessarily consist of the vinyl extension (which had been treated with the acrylic-adhesive mixture). After a few reinforcement sessions, however, each of which take place once every four weeks, the vinyl extension has grown off and the tip of the nail is the individual's natural nail with only the cyanoacrylate adhesive-acrylic powder mixture on it.

Following the drilling of the nail tip with an electric nail drill, the thickness (i.e. depth) of the nail (the part with the old coatings of adhesive-acrylic mixture), not including the natural nail that has grown in since the last session, is shaved or thinned down by an electric nail drilling. At that point, the method of the present invention used for the initial treatment session is followed so that coatings of adhesive and powder are applied to the entire nail surface (the entire surface of the natural nail plus that of any vinyl extension that remains) except that only two coatings on top and one coating on the underside of the nail are employed. With reinforcement sessions for the prefabricated nail the number of coatings is less fixed. Use as many coatings as necessary to obtain the thickness desired by the wearer.

SHIELDS—NO VINYL APPLIED

Some people who have reasonably long nails and do not want a vinyl or other nail extension may obtain the benefits of the present invention without requesting a vinyl extension. Instead they would use the adhesive and powder treatment of the present invention to employ a shield on their nails. This would be done without vinyl and it would be done in almost exactly the same way the reinforcement treatments are provided. Instead of applying vinyl extension the wearer simply begins the nail treatment by applying the cyanoacrylate adhesive of the present invention followed by the acrylic powder mixture (with sodium bicarbonate) of the present invention to the entire existing natural nail. The difference between a shield and a reinforcement treatment is the number of coatings—a shield employs four coatings on the top surface of the nail and two on the bottom surface. Also, with a shield in contrast to a reinforcement treatment, the preliminary steps of shortening and drilling (before application of the adhesive) are not done.

MENDING CRACKED OR BROKEN NAILS—VINYL PATCH

Some people who have broken or cracked nails but do not want or need a vinyl or other nail extension and cannot suffice with a shield can still obtain the benefits of the present invention by utilizing a vinyl nail patch. The method and materials associated with the vinyl nail patch are the same as the method and materials associated with the vinyl extension. The difference is only that instead of applying a "full" vinyl extension at the top of the nail (as in FIG. 2) you apply a rectangular vinyl patch large enough to surround the entire crack in the nail. The patch is cut by scissors off the same roll as the vinyl extension and same adhesive and powder are used. Since there was a crack or gap, enough adhesive is applied under the patch at the outset of the treatment to fill in the gap or crack. After the vinyl is applied, the procedure for a regular reinforcement treatment is followed except that before a first coating of adhesive is applied to the entire nail surface, you drill the edges of the vinyl patch with any commercially available device such as a carbide cutter or other appropriate electric nail drill with a hard bit so that there should no longer be a bump on the fingernail at the edges of the vinyl patch but rather a smooth surface at the transition point. This is like Step Four of the regular treatment (with vinyl extension).

DETAILED DESCRIPTION OF THE DRAWINGS

Figures 1, 2, 3, 4, 5, 6:
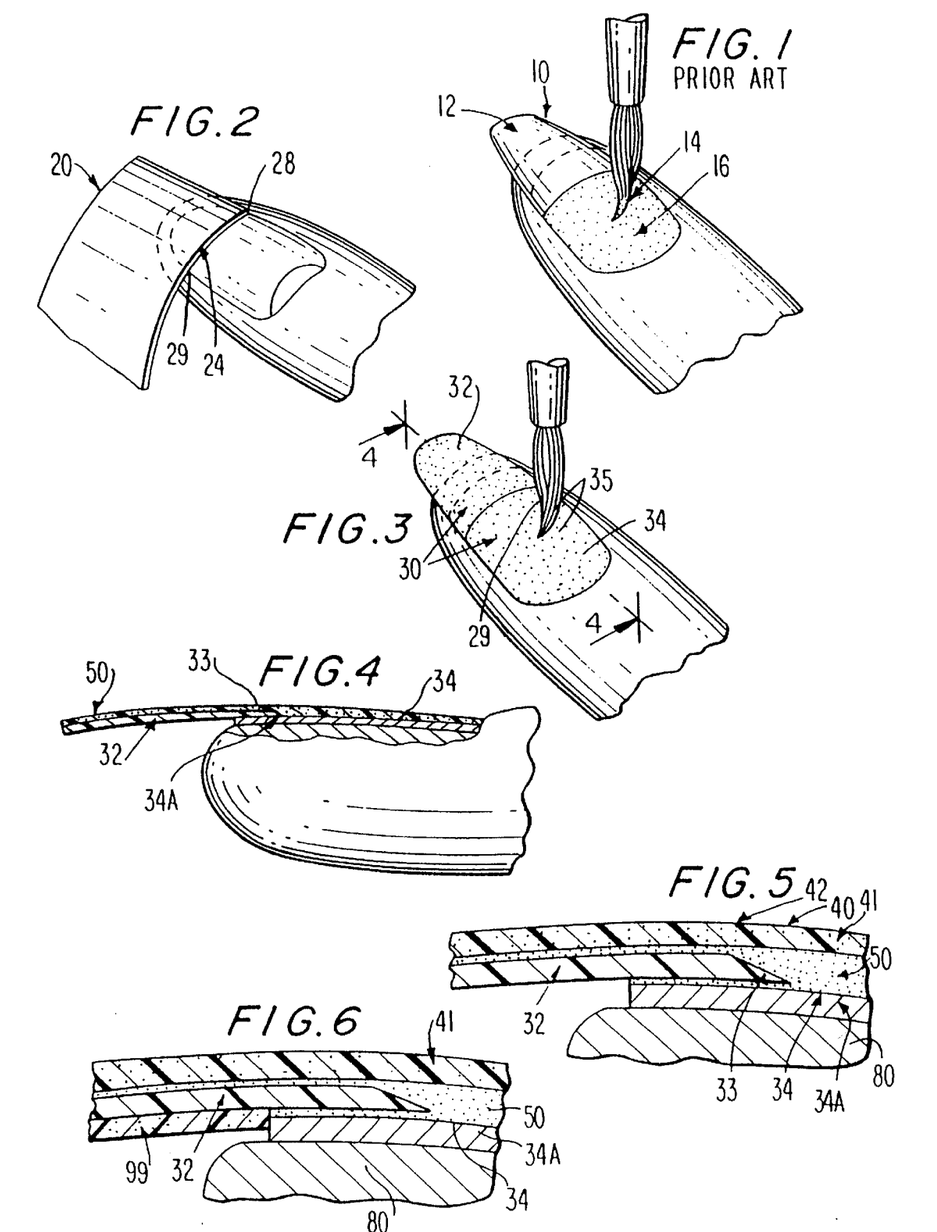
FIG. 1 is a perspective view illustrating a prior art procedure wherein the adhesive is applied rearward of the nail extension.
FIG. 2 is a plan view of a novel vinyl nail extension of the present invention applied to a fingernail.
FIG. 3 is a plan view illustrating the adhesive layer on the natural fingernail in preparation for the artificial nail employing the novel composition and method of the present invention.
FIG. 4 is a sectional elevation view taken substantially along the line 4—4 of FIG. 3 showing the nail after the cyanoacrylate adhesive has been added.
FIG. 5 is an expanded sectional view of the top part of FIG. 4 showing the hardened new nail after both the adhesive and the acrylic powder mixture have been added.
FIG. 6 is an expanded sectional view of the top part of FIG. 4 showing the hardened new nail after both the adhesive and the acrylic powder mixture have been added including on the underside of the nail extension.

FIG. 1 depicts the prior art artificial fingernail 10 described in U.S. Pat. No. 4,450,848 to Ferrigno. In FIG. 1, a plastic extension or tip 12 is adhered to the end of the natural fingernail. FIG. 1 shows the method employed in Ferrigno whereby liquid cyanoacrylate adhesive 14 is then applied to the top surface 16 of the natural fingernail only rearward of the tip 12. Following this, a standard acrylic ester copolymer in powder form is also applied and allowed to dry. In Ferrigno, the form used on the tip (extension) is made of acetate plastic. Other methods of the prior art include the application of adhesive to the top surface of a natural fingernail and to the top surface of a fingernail extension.

FIG. 2 depicts the vinyl extension or tip 20 of the present invention. Before attaching the vinyl extension follow Step One of the method of the present invention wherein the natural fingernail is prepared for the artificial nail extension in that any dead skin around the cuticles that extend over the natural nail is removed by routine methods such as by lightly drilling the cuticle area with a small diamond bit and then, in Step Two, cyanoacrylate adhesive is applied to the free edge of the natural fingernail by means of a nail polish brush or similar applicator enough to cover the area where the vinyl extension will be placed, namely approximately one-third of the height of the natural nail.

In FIG. 2, the vinyl extension is attached to the end of the natural fingernail by placing a 12 inch long and ½ to ⅝ inch wide roll of frosty clear firm polyvinyl chloride having a thickness of approximately 10 mils on top of the end portion of the natural fingernail containing the adhesive. The vinyl in this example is a polyvinyl chloride with low amounts per million of a plasticizer and a metallic stabilizer. The thickness of the vinyl in this example can range from 8 to 12 mils and 10 mils is ideal (as indicated earlier 3–8 or 12–20 mils will work but not necessarily as well). Using scissors, the vinyl is then cut off the roll and trimmed to fit the size of the fingernail tip. The bottom edge of the vinyl should extend over approximately one-third of the height of the natural nail and should generally correspond to an imaginary line across the nail connecting the points 28, 29 on the perimeter of the natural nail where the "whites" of the nail end. The bottom edge 24 of the vinyl extension (the edge overlapping the natural nail) is then drilled with any commercially available device such as a carbide cutter or other appropriate electric drill with a hard bit so that there is no longer a bump on the fingernail at the beginning of the vinyl fingernail extension but rather a smooth surface at the transition point. As indicated before, one of the advantages of vinyl over acetate plastic or other hard plastic used in the prior art is that the necessary thickness of ten mils can be maintained while at the same time retaining the soft pliability of the vinyl. In contrast, ten mil plastic is hard and not very pliable. In addition, plastic that is thin enough to be soft is not thick enough to develop into hard nails in accordance with the method and composition of the present invention. FIG. 3 illustrates the application of the cyanoacrylate adhesive 35 onto the entire nail 30 including the vinyl extension 32 and the natural nail surface 34.

FIG. 4 is a sectional elevation view taken substantially along the line 4—4 of FIG. 3 after the cyanoacrylate adhesive has been added but before the acrylic powder mixture has been sprayed on with a non-aerosol or an aerosol spray. The adhesive layer 50 is applied on the vinyl extension 32 and on the natural nail surface 34 of natural nail 34A.

FIG. 5 is an expanded sectional view of the top part of FIG. 4 showing the hardened new nail after both the adhesive layer 50 and the acrylic powder mixture 41 have been added. As can be seen, after the application of the acrylic powder mixture the entire surface of the nail 40 is smooth and the vinyl extension, natural nail, adhesive and acrylic powder form a single integrated unit. There is no surface protrusion at the area 42 where the vinyl nail extension meets the natural nail. This is due in part to the smoothed bottom edge 33 of the vinyl extension 32 that meets the top nail surface 34 of natural fingernail 34A that sits on finger 80.

FIG. 6 is an expanded sectional view of the top part of FIG. 4 showing the hardened new nail after both the adhesive and the acrylic powder mixture have been added including a layer 99 on the underside of the nail extension 32. Natural fingernail 34A sits on finger 80.

Figure 7A:
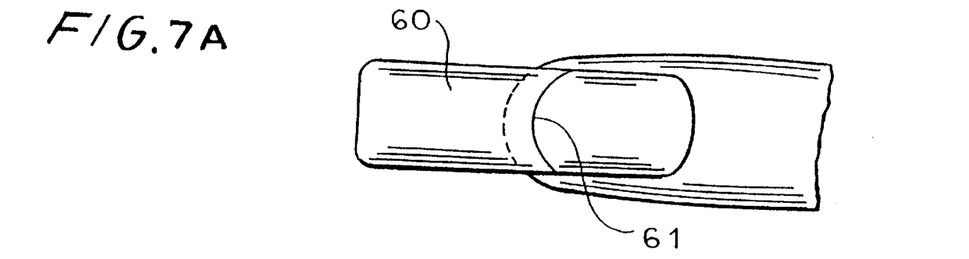
FIGS. 7A, 7B and 7C are top plan views of different available shapes for the prefabricated vinyl extension of the present invention applied to a fingernail.
Figure 7B:
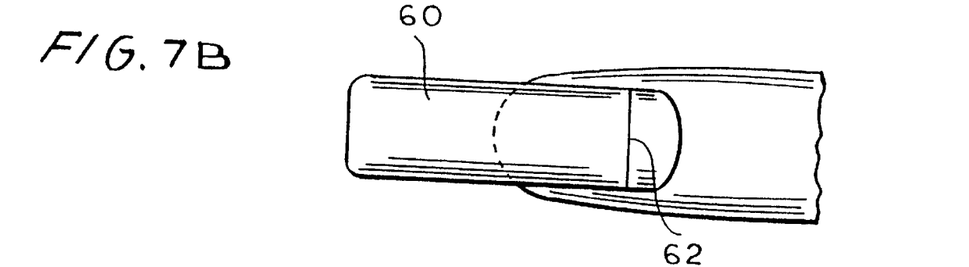
Figure 7C:
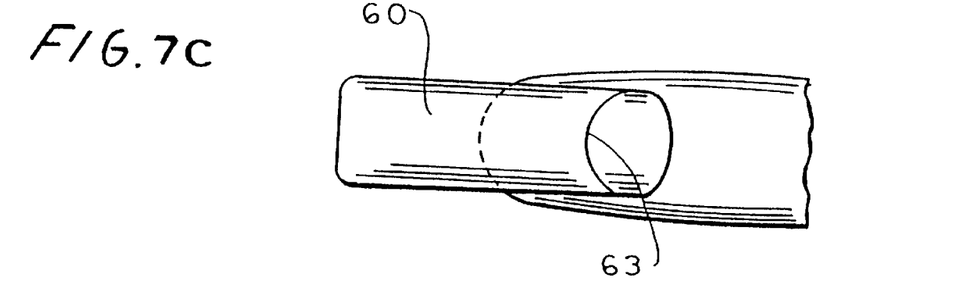

FIGS. 7A, 7B and 7C are top plan views of different available shapes for the prefabricated vinyl extension of the present invention applied to a fingernail. FIGS. 7A and 7C show the rounded arcuate bottom edge 61 and 63 respectively and FIG. 7B shows the straight bottom edge 62 of the prefabricated vinyl extension 60.

FIG. 8 is a top plan view of the prefabricated vinyl extension of FIG. 7A after the "fill in" layer of nail composition of the present invention has been applied to the natural nail 66.

FIG. 9 is an enlarged sectional view taken along line 9—9 of FIG. 8. The style of prefabricated nail in FIG. 9 is that of FIG. 7A where the nail extension has been manufactured so that it is thinner than normal (i.e. thinner than 6–10 mils or other chosen thickness) at the portion 72 of the nail extension covering the natural nail. The remainder of the nail extension 73 that extends outward from the finger is the normal thickness (i.e. approximately 6–10 mils or other chosen thickness) of the vinyl and this extra thickness appears in the underside of the extension 73a.

DESCRIPTION OF EXAMPLES

The composition of the present invention will be more fully described by reference to the following examples. Parts are by weight unless otherwise specified.

Example I

A nail composition made of a mixture of sodium bicarbonate powder and acrylic powder wherein the ratio by volume of the powder is 6 parts acrylic powder to 1 part sodium bicarbonate. The sodium bicarbonate is placed in a grinding machine and ground into a fine powder before mixing with the acrylic powder. When using other sodium compounds (sodium sulfate, sodium carbonate or sodium borate) in place of sodium bicarbonate the granules may not break up as easily into fine powder. The acrylic powder used in this mixture is as formulated as follows:

| Ingredient | Percent |
| --- | --- |
| acrylic ester copolymer | 98.7% |
| e.g. methyl methacrylate polymer | (50% of copolymer) |
| e.g. ethyl methacrylate polymer | (50% of copolymer) |
| benzoyl peroxide | approximately 1.0% |
| titanium dioxide | approximately 0.1% |
| silicon dioxide | approximately 0.1% |
| Reddening agent (optional) | approximately 0.1% |

Example II

| Ingredient | Percent |
| --- | --- |
| acrylic ester copolymer | 98.9% |
| e.g. methyl methacrylate polymer | (70% of copolymer) |
| e.g. ethyl methacrylate polymer | (30% of copolymer) |
| benzoyl peroxide | approximtately 0.8% |
| titanium dioxide | approximtately 0.1% |
| silicon dioxide | approximately 0.1% |
| Reddening agent (optional) | approximately 0.1% |

In examples I and II the benzoyl peroxide has varied from 0.8 to 1.0 per cent by weight of the acrylic powder and the proportion of polymers in the acrylic ester copolymer has been varied.

Example III

A nail composition made of a mixture of sodium bicarbonate powder and acrylic powder wherein the ratio by volume of the powder is 10 parts acrylic powder to 1 part sodium bicarbonate. The sodium bicarbonate is placed in a grinding machine and ground into a fine powder to which optionally is added 0.1% by volume reddening agent, for example D & C red dye no. 33, before mixing with the acrylic powder. When using other sodium compounds (sodium sulfate, sodium carbonate or sodium borate) in place of sodium bicarbonate the granules may not break up as easily into fine powder. The acrylic powder used in this mixture is as formulated as follows:

| Ingredient | Percent |
| --- | --- |
| acrylic ester polymers | 98.9% |
| e.g. methyl methacrylate polymer | |
| benzoyl peroxide | approximately 0.8% |
| titanium dioxide | approximately 0.1% |
| silica | approximately 0.1% |
| reddening agent (optional) | approximately 0.1% |

Example IV

A nail composition adhesive as formulated as follows:

| Ingredient | Percent |
| --- | --- |
| ethyl cyanoacrylate | greater than 99% |
| preservative | less than 1% |

In Examples I, II, III the benzoyl peroxide is merely illustrative of any suitable catalyst or initiator for the polymerization reaction that occurs upon adding the acrylic powder mixture to the adhesive. The titanium dioxide and the silicon dioxide (or silica) are simply opaquing agents for the powder. The reddening agent, for example D & C red dye no. 33, has been added to the acrylic powder even though the sodium bicarbonate, as explained below, contains the same reddening dye. It should be clear that the reddening agent is only optional. The purpose of the optional reddening dye that is added to the acrylic powder is to make the sodium bicarbonate (when added to the acrylic powder) pink in a homogeneous manner, since sodium bicarbonate is naturally white. The result leaves the nails with a natural-looking pinkish pigmentation.

The acrylic ester copolymers (or polymers) are mixed together with the benzoyl peroxide, titanium dioxide, silicon dioxide and reddening dye using known standard methods of mixing such compounds such as described in standard chemistry books. Alternatively, the acrylic powder mixture (without any sodium compound) of Examples I and II can be purchased from a company such as OPI Products, Inc. of North Hollywood, Calif. already mixed. The acrylic powder mixture (without any sodium compound) of Example III can be purchased from various other companies (e.g. under the product name Nail Touch) already mixed. In either case, the following procedure at room temperature and normal pressure is one method, albeit primitive, that can be used to create the final powder mixture but the present invention is in no way limited to a particular method of preparing the powder mixture.

The sodium bicarbonate, which comes in the form of white granules, is placed in a grinding machine or other device where it can be ground. It is then ground to fine powder. Then, optionally, approximately 1 part per 5000 by volume reddening agent, such as D & C red dye no. 33, is added to the sodium bicarbonate and again mixed by the grinding machine or other mixing device in order to make the sodium bicarbonate powder slightly pink. The acrylic powder (without the sodium compound) is mixed together in a way that creates a homogeneous mixture. It is suggested, only as an example, that this can be accomplished as follows: the acrylic powder (without the sodium compound) is mixed together with the sodium bicarbonate by first scooping a predetermined volume of the acrylic powder and placing it in a container and then adding one tenth that volume of the finely ground and reddened sodium bicarbonate powder and then mixing them together with a stirring stick or grinding machine for a specified time to create one half the amount of powder desired. Then scoop out the same volume of acrylic powder as before and the same volume of sodium bicarbonate as before (maintaining the same 10 to 1 ratio) adding them to the mixture in the same order and them mixing again. It is suggested although not required that by thus first creating a mixture of half the powder amount desired and then repeating the procedure to obtain another half, that homogeneity is maximized.

In all cases, although the ratio of the ingredients of the powder used in the present invention have been described herein in terms of mixtures by volume, it is possible and in fact it may be more precise to describe such mixtures by weight.

Although the invention has been described in detail in the foregoing specification along with the accompanying drawing with respect to various embodiments thereof, these are intended to be illustrative only and not limiting. One skilled in the art will recognize that various modifications and variations may be made therein which are within the spirit of the invention and the scope of the appended claims.

What is claimed is:

1. A foundation for an artificial fingernail extension comprising polyvinyl chloride having a tensile strength of between approximately 3500 psi and 10,000 psi and which is between approximately 6 and 50 mils thick.

2. The foundation of claim 1, wherein it is between approximately 10 and 30 mils thick.

3. The foundation of claim 1, wherein it is frosty clear.

4. An artificial fingernail for coating human fingernails comprising a rigid prefabricated polyvinyl chloride fingernail extension overlapping a natural fingernail and at least one layer of an adhesive on the natural fingernail and on the prefabricated polyvinyl chloride fingernail extension that forms a permanent bond with the polyvinyl chloride.

5. The artificial fingernail of claim 4, wherein the prefabricated polyvinyl chloride fingernail extension has a thickness between approximately 6 and 50 mils.

6. The artificial fingernail of claim 4, wherein the polyvinyl chloride fingernail extension is frosty clear.

7. The artificial fingernail of claim 4, wherein the polyvinyl chloride fingernail extension is between approximately 10 and 30 mils thick.

8. The artificial fingernail of claim 4, wherein the adhesive is cyanoacrylate adhesive.

9. The artificial fingernail of claim 4, wherein the adhesive is urethane acrylate gel.

10. An artificial nail for coating human nails comprising a rigid prefabricated polyvinyl chloride fingernail extension overlapping a natural fingernail, a layer of cyanoacrylate adhesive on the natural fingernail and a layer of a mixture in powder form of acrylic ester polymers and sodium bicarbonate over the layer of cyanoacrylate adhesive, at least one additional layer of cyanoacrylate adhesive on the polyvinyl chloride fingernail extension and on the natural fingernail wherein each such additional layer of cyanoacrylate adhesive has on it an additional layer of a mixture in powder form of acrylic ester polymers and sodium bicarbonate.

11. The artificial nail of claim 10, wherein the mixture in powder form is between approximately 1 to 15 parts by volume acrylic ester polymers and 1 part sodium bicarbonate.

12. The artificial nail of claim 10, wherein the mixture in powder form is between approximately 8 to 12 parts by volume acrylic ester polymers and 1 part sodium bicarbonate.

13. The artificial nail of claim 10, wherein one member of the group selected from sodium sulfate, sodium carbonate, sodium borate, aluminum stearate, ammonium acetate, sodium sesquicarbonate, aluminum hydroxide, sodium carboxyl methyl cellulose, sodium acetate and ammonium carbonate replaces sodium bicarbonate.

14. An artificial nail composition for use with human nails comprising a layer of cyanoacrylate adhesive and a layer of a mixture in powder form of acrylic ester polymers and sodium bicarbonate.

15. The composition of claim 14, wherein the mixture in powder form is between approximately 1 and 15 parts by volume acrylic ester polymers and 1 part sodium bicarbonate.

16. The composition of claim 14, wherein the mixture in powder form is between approximately 8 and 12 parts by volume acrylic ester polymers and 1 part sodium bicarbonate.

17. An artificial nail composition for use with human nails comprising a layer of a mixture in powder form of acrylic ester polymers and sodium bicarbonate.

18. The composition of claim 17, wherein the mixture in powder form is between approximately 1 and 15 parts by volume acrylic ester polymers and 1 part sodium bicarbonate.

19. The composition of claim 17, wherein the mixture in powder form is between approximately 8 and 12 parts by volume acrylic ester polymers and 1 part sodium bicarbonate powder.

20. The composition of claim 17, wherein one member of the group selected from sodium sulfate, sodium carbonate, sodium borate, aluminum stearate, ammonium acetate, sodium sesquicarbonate, aluminum hydroxide, sodium carboxyl methyl cellulose, sodium acetate and ammonium carbonate replaces sodium bicarbonate.

21. A method of shielding an artificial fingernail on a natural fingernail, comprising the steps of:
   a. applying a coating of cyanoacrylate adhesive to the top surface of the natural fingernail;
   b. applying a layer of a mixture in powder form of between 1 and 15 parts by volume acrylic ester polymers and 1 part sodium bicarbonate to the top surface of the natural fingernail on the adhesive coating while said adhesive coating is still wet to cause instant hardening;
   d. repeating steps b. and c. three times after brushing off excess powder before each repetition; and
   e. shaping and filing a resulting fingernail surface.

22. The method of claim 21, wherein the mixture in powder form is between 8 and 12 parts by volume acrylic ester polymers and 1 part sodium bicarbonate.

23. The method of claim 21, wherein one member selected from the group consisting of sodium sulfate, sodium carbonate, sodium borate, aluminum stearate, ammonium acetate, sodium sesquicarbonate, aluminum hydroxide, sodium carboxyl methyl cellulose, sodium acetate and ammonium carbonate replaces sodium bicarbonate.

24. A custom fitted artificial nail for coating human nails comprising a frosty clear polyvinyl chloride fingernail extension overlapping a natural fingernail, a layer of cyanoacrylate adhesive on the polyvinyl chloride fingernail extension and on the natural fingernail and a layer of a mixture in powder form of acrylic ester polymers and sodium bicarbonate over the layer of cyanoacrylate adhesive.

25. The artificial nail of claim 24, wherein the mixture in powder form is between 1 and 15 parts by volume acrylic ester polymers and 1 part sodium bicarbonate.

26. The artificial nail of claim 24, wherein the polyvinyl chloride fingernail extension is between 3 and 20 mils thick and is firm.

27. The artificial nail of claim 24, wherein the mixture in powder form is between 1 and 15 parts by volume acrylic ester polymers and 1 part a member of the group selected from sodium sulfate, sodium carbonate, sodium borate, aluminum stearate, ammonium acetate, sodium sesquicarbonate, aluminum hydroxide, sodium carboxyl methyl cellulose, sodium acetate and ammonium carbonate.

28. A custom fitted artificial fingernail for coating human fingernails comprising a firm polyvinyl chloride fingernail extension overlapping a natural fingernail and at least one layer of an adhesive on the natural fingernail and on the polyvinyl chloride fingernail extension that forms a permanent bond with the polyvinyl chloride.

29. The artificial fingernail of claim 28, wherein the adhesive is cyanoacrylate adhesive.

30. The artificial fingernail of claim 28, wherein the polyvinyl chloride fingernail extension has a thickness of approximately 3 to 20 mils.

31. The artificial fingernail of claim 28, wherein the polyvinyl chloride fingernail extension has a thickness of approximately 8 to 12 mils.

32. The artificial fingernail of claim 28, wherein the polyvinyl chloride fingernail extension is frosty clear.

33. The artificial fingernail of claim 28, wherein the polyvinyl chloride fingernail extension is frosty clear and is between 8 and 12 mils thick.

34. An artificial nail composition for use with human nails comprising a layer of cyanoacrylate adhesive and a layer of a mixture in powder form of between 1 and 15 parts by volume acrylic ester polymers and 1 part sodium bicarbonate.

35. The composition of claim 34, wherein one member of the group selected from sodium sulfate, sodium carbonate, sodium borate, aluminum stearate, ammonium acetate, sodium sesquicarbonate, aluminum hydroxide, sodium carboxyl methyl cellulose, sodium acetate and ammonium carbonate replaces sodium bicarbonate.

36. An artificial nail composition for use with human nails comprising a layer of a mixture in powder form of between 1 and 15 parts by volume acrylic ester polymers and 1 part sodium bicarbonate.

37. The composition of claim 36, wherein one member of the group selected from sodium sulfate, sodium carbonate, sodium borate, aluminum stearate, ammonium acetate, sodium sesquicarbonate, aluminum hydroxide, sodium carboxyl methyl cellulose, sodium acetate and ammonium carbonate replaces sodium bicarbonate.

38. An artificial fingernail extension used for forming an artificial fingernail on a natural nail, comprising firm polyvinyl chloride whose thickness is approximately in the range of 3 to 20 mils thick.

39. The artificial fingernail extension of claim 38, wherein the polyvinyl chloride is frosty clear.

40. An artificial fingernail extension used for forming an artificial fingernail on a natural nail, comprising firm polyvinyl chloride whose thickness is approximately in the range of 8 to 12 mils thick.

41. The artificial fingernail extension of claim 40, wherein the polyvinyl chloride is frosty clear.

42. A foundation for an artificial fingernail extension comprising rigid prefabricated polyvinyl chloride having a tensile strength of between approximately 3500 psi and 10,000 psi.

* * * * *